United States Patent
Nanba et al.

(10) Patent No.: US 9,845,453 B2
(45) Date of Patent: Dec. 19, 2017

(54) CELL CULTURE APPARATUS AND CELL CULTURE METHOD

(71) Applicant: HITACHI, LTD., Tokyo (JP)

(72) Inventors: Masaru Nanba, Tokyo (JP); Ryouichi Haga, Tokyo (JP); Sei Murakami, Tokyo (JP); Haruo Suzuki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/909,277

(22) PCT Filed: Aug. 1, 2014

(86) PCT No.: PCT/JP2014/070371
§ 371 (c)(1),
(2) Date: Feb. 1, 2016

(87) PCT Pub. No.: WO2015/033715
PCT Pub. Date: Mar. 12, 2015

(65) Prior Publication Data
US 2016/0186123 A1    Jun. 30, 2016

(30) Foreign Application Priority Data
Sep. 9, 2013   (JP) .................. 2013-186430

(51) Int. Cl.
*C12M 1/34*    (2006.01)
*C12M 3/00*    (2006.01)
(Continued)

(52) U.S. Cl.
CPC ............ *C12M 41/30* (2013.01); *C12M 23/14* (2013.01); *C12M 23/22* (2013.01); *C12M 23/26* (2013.01); *C12M 37/00* (2013.01); *C12M 41/36* (2013.01)

(58) Field of Classification Search
CPC ...... C12M 23/14; C12M 23/22; C12M 23/26; C12M 37/00; C12M 41/30; C12M 41/36
See application file for complete search history.

(56) References Cited

U.S. PATENT DOCUMENTS

2007/0037276 A1    2/2007   De Crecy
2008/0220501 A1    9/2008   De Crecy
(Continued)

FOREIGN PATENT DOCUMENTS

EP    2407533 A1    1/2012
JP    H03-10677 A   1/1991
(Continued)

OTHER PUBLICATIONS

Castro, Guillermo R. et al., "Modelling and Operation of a Turbidity-Meter for On-Line Monitoring of Microbial Growth in Fermenters.", Process Biochemistry, vol. 30, No. 8, pp. 768-772, (1995).
(Continued)

*Primary Examiner* — Nathan Bowers
*Assistant Examiner* — Lydia Edwards
(74) *Attorney, Agent, or Firm* — Oliff PLC (57) ABSTRACT

A cell culture apparatus is provided which can continuously and accurately measure turbidity of a cell culture solution and culture a cell, without inserting a turbidity sensor from outside into a sterile bag. The cell culture apparatus includes: a flexible and transparent sterile bag that is installed at a prescribed position in the cell culture apparatus and in which a cell contained in a cell culture solution is cultured; and a turbidity sensor that includes a light emitter which emits light to the cell culture solution in the sterile bag via a portion of the sterile bag, a light receiver which receives the light transmitted through the cell culture solution via another portion of the sterile bag, and that is configured to place the light emitter, the portion of the sterile bag, another portion of the sterile bag, and the light receiver, optically on a same straight line.

14 Claims, 4 Drawing Sheets

(51) Int. Cl.
C12M 1/00 (2006.01)
C12M 1/12 (2006.01)

(56) References Cited

U.S. PATENT DOCUMENTS

| | | | | |
|---|---|---|---|---|
| 2011/0318725 | A1* | 12/2011 | Suenaga | C12M 23/14 435/3 |
| 2012/0327404 | A1 | 12/2012 | Olesen | |
| 2013/0078733 | A1* | 3/2013 | Holmes | B01L 3/0217 436/174 |
| 2014/0011186 | A1 | 1/2014 | Suenaga et al. | |

FOREIGN PATENT DOCUMENTS

| | | |
|---|---|---|
| JP | H05-68533 A | 3/1993 |
| JP | 2007-282629 A | 11/2007 |
| JP | 2009-544323 A | 12/2009 |
| JP | 2012-189386 A | 10/2012 |
| JP | 2013-521477 A | 6/2013 |
| WO | 2010/103748 A1 | 9/2010 |
| WO | 2012/127650 A1 | 9/2012 |

OTHER PUBLICATIONS

Nov. 4, 2014 Search Report issued in International Patent Application No. PCT/JP2014/070371.
Mar. 23, 2017 Extended Search Report issued in European Patent Application No. 14842701.6.

* cited by examiner

CELL CULTURE APPARATUS AND CELL CULTURE METHOD

CROSS REFERENCE TO RELATED APPLICATION

This application is a National Stage Application of PCT/JP 2014/070371, filed on Aug. 1, 2014, and which application is incorporated herein by reference. To the extent appropriate, a claim of priority is made to the above disclosed application.

TECHNICAL FIELD

The present invention relates to a cell culture apparatus and a cell culture method.

BACKGROUND ART

In a cell culture apparatus in which microorganisms, animal or plant cells, or the like are cultured, a state of cultured cells is monitored so as to efficiently culture the target cells while controlling flow stirring or gas vent in a culture vessel or supply of a liquid medium. Other items to be monitored include a culture temperature, a pH, a dissolved oxygen concentration, a dissolved carbon dioxide concentration, a cell concentration, a medium component such as amino acid including glucose and glutamine, a metabolic component of the cell such as lactic acid and amino acid, and a cellular product such as protein.

If the culture vessel used is made of stainless steel or glass, an electrode type measurement sensor suited for the culture temperature, pH, dissolved oxygen concentration, and dissolved carbon dioxide concentration of the monitoring items described above is installed on a roof in an upper part of the culture vessel or on a wall surface thereof, so as to monitor the culture condition.

The medium component, the metabolic component, the cellular product, or the like is measured by sampling part of the cell culture solution in the culture vessel under a bacteria-free condition and measuring the target item using an appropriate measurement unit.

The cell concentration is typically calculated by counting the number of cells using a sampled cell culture solution or by measuring light turbidity. Similarly to the above-described electrode type measurement sensor, a probe type turbidity sensor which is used by being inserted in a culture vessel is currently in practical use and can also be used for monitoring the cell concentration.

When the electrode type measurement sensor is used, before starting a culture of cells, it is necessary for the electrode type measurement sensor to be subjected to sterilization in an autoclave in a state where the sensor is set in a culture vessel, or by circulating steam in a stationary culture vessel. When the cell culture solution is sampled, it is necessary for extract piping of the cell culture solution to be subjected to sterilization using steam, flame, alcohol, or the like each time.

Given these circumstances, in order to quickly set up a cell culture apparatus, facilitate an operation of sampling, reduce cost, and the like, a single-use system using a flexible vessel made of plastic has been currently developed and put to practical use, in place of a conventional stainless steel or glass culture vessel.

In a culture using the single-use system, a sterile bag is previously sterilized with ethylene oxide gas or gamma radiation. A sterilized liquid medium and a cell to be cultured are then put into the sterile bag. Also in the single-use system as described above, a very small quantity of the cell culture solution in the sterile bag is sampled under the bacteria-free condition at fixed time intervals; and an externally-provided analyzer measures the pH, dissolved oxygen concentration, carbon dioxide concentration, a cell concentration, and the like of the cell culture solution, so as to monitor a state of cultured cells in the culture vessel.

Such an operation of monitoring using the single-use system involves a risk of contamination and a loss of the cell culture solution. If continuous monitoring is necessary, such an operation is thus not always appropriate. Hence, there is a need for developing measurement technology in which the above-mentioned various measurement sensors are suitably adapted to the single-use system. For example, when continuous monitoring is required, a chip type fluorescent sensor is used in which: a fluorescent chip having fluorescent dye whose color development changes depending on the pH, dissolved oxygen concentration, or carbon dioxide concentration of the cell culture solution, is placed in a sterile bag; and fluorescence is detected and measured using an optical means from outside of the sterile bag.

Nonetheless, the turbidity sensor which is mainly used for measuring a cell concentration based on turbidity is of the aforementioned type used by being inserted in a culture vessel. Further, almost all types of the turbidity sensor are suited to being used with a culture vessel made of stainless steel or glass. There is thus need for developing a turbidity sensor usable in the single-use system and also developing a cell culture apparatus making use of the turbidity sensor. The inventions directed to such technologies are described in, for example, Patent Documents 1 to 3.

Japanese Laid-Open Patent Application, Publication No. H03-10677 (to be referred to as Patent Document 1 hereinafter) discloses a culture bag into which a cell and a culture medium are put to be cultured therein. The culture bag includes: a bag main body for receiving the cell and the culture medium; and an optical sensor which is placed in the bag main body and optically detects a concentration of the cells in the bag main body.

Japanese Laid-Open Patent Application, Publication No. 2012-189386 (to be referred to as Patent Document 2 hereinafter) discloses a component analyzer which includes: an adjustment device that adjusts a thickness of a flexible container as a target to be measured; and a measuring device that has a function of emitting near infrared light and a function of receiving the emitted near infrared light. The adjustment device includes a first adjustment part and a second adjustment part which adjust a thickness of an outer portion of the flexible container, the outer portion being a portion nearer to an edge of the flexible container with respect to a central portion thereof. The thickness of the outer portion of the flexible container is adjusted in such a manner that a first measuring surface contacts an outer portion of a first surface of the flexible container and a second measuring surface of the second adjustment part contacts an outer portion of a second surface of the flexible container. The measuring device has a function of emitting near infrared light from the first measuring surface toward the second measuring surface and a function of receiving the near infrared light at the second measuring surface.

International Publication No. WO 2012/127560 pamphlet (to be referred to as Patent Document 3 hereinafter) discloses a turbidity measurement device for measuring turbidity of a culture solution from outside a culture tank. The turbidity measurement device includes: a transparent part provided in a tank wall of a culture tank; a reflecting mirror disposed in a culture solution in the culture tank; a light emitter for irradiating light to the reflecting mirror via the transparent part, the light emitter being disposed outside the culture tank; and a detecting light receiver for receiving light from a direction of the reflecting mirror via the transparent part, the detecting light receiver being disposed outside the culture tank. The device described in Patent Document 3 measures turbidity by: disposing the reflecting mirror in the culture tank; irradiating light from the light emitter disposed outside the culture tank to the reflecting mirror; and detecting the reflected light having been reflected on the reflecting mirror, by the light receiver.

RELATED ART DOCUMENTS

Patent Documents

Patent Document 1: Japanese Laid-Open Patent Application, Publication No. H03-10677
Patent Document 2: Japanese Laid-Open Patent Application, Publication No. 2012-189386
Patent Document 3: International Publication No. WO 2012/127650 pamphlet

SUMMARY OF THE INVENTION

Problems to be Solved by the Invention

As described above, the device disclosed in Patent Document 1 detects a concentration of the cells using the optical sensor disposed in the culture bag main body. That is, a pair of optical fibers connected to the optical sensor penetrate through an outer wall of the culture bag. This can reduce mechanical strength of a portion through which the optical sensor penetrate and increase a risk of contamination when the cell culture solution is shaken or flow stirred.

The component analyzer disclosed in Patent Document 2 is a so-called one-dimensional flat sterile bag. If the bag is applied to cell culturing, a light path for near-infrared light disadvantageously contains gas phase, which makes it difficult to accurately measure the turbidity.

The turbidity measurement device disclosed in Patent Document 3 is assumed to be used in a stainless steel or glass culture tank. Patent Document 3 thus discloses that the reflecting mirror is installed on a device such as a baffle plate, a pipe, an electrode member, or a dedicated support member, each of which is placed in the culture tank. In case of a sterile bag for the single use, however, such a support member as described above cannot be arranged therein. This makes it difficult to install the reflecting mirror. Further, the invention described in Patent Document 3 structurally has difficulty in stirring a cell culture solution present between a culture tank and a reflecting mirror. This makes it difficult to accurately measure turbidity because fragments of cells or intracellular proteins in a cell culture solution easily adhere onto a surface of the reflecting mirror as contaminants.

Patent Document 3 describes that a technical idea thereof is applicable to a one-dimensional single-use culture tank used by shaking and stirring a flat sterile bag (a horizontally-long transparent bag). More specifically, Patent Document 3 describes that turbidity can be measured in such a manner that a reflecting mirror is fixed and appropriately arranged inside a transparent part placed on a bottom wall of the horizontally-long bag via a support member firmly fixed to an inner wall of the bag using an adhesive or the like. In the manner, however, it is difficult to stir the cell culture solution present between the reflecting mirror and a tank wall of the sterile bag. This makes it difficult to accurately measure turbidity because fragments of cells or intracellular proteins in a cell culture solution easily adhere onto a surface of the reflecting mirror as contaminants.

The present invention has been made in light of the problems described above and in an attempt to provide a cell culture apparatus and a cell culture method, each of which can continuously and accurately measure turbidity of a cell culture solution and culture the cell, without inserting a turbidity sensor from outside into a sterile bag.

Means for Solving the Problem

A cell culture apparatus includes: a flexible and transparent sterile bag that is installed at a prescribed position in the cell culture apparatus and in which a cell contained in a cell culture solution is cultured; and a turbidity sensor that includes a light emitter which emits light to the cell culture solution in the sterile bag via a first portion of the sterile bag, a light receiver which receives the light transmitting through the cell culture solution in the sterile bag via a second portion of the sterile bag, and that is configured to place the light emitter, the first portion of the sterile bag, the second portion of the sterile bag, and the light receiver, optically on a same straight line.

A cell culture method includes: a setting step that is a step of setting, in respective prescribed positions in a cell culture apparatus, a flexible and transparent sterile bag, and a turbidity sensor that includes a light emitter which emits light to a cell culture solution containing a cell to be cultured in the sterile bag via a first portion of the sterile bag and a light receiver which receives the light transmitting through the cell culture solution in the sterile bag via a second portion of the sterile bag, and that is configured to place the light emitter, the first portion of the sterile bag, the second portion of the sterile bag, and the light receiver, optically on a same straight line; and a culture step that is a step of putting and culturing the cell culture solution inside the sterile bag having been set in the setting step. In the culture step, light is emitted from the light emitter of the turbidity sensor to the cell culture solution, and the light having transmitted through the cell culture solution is received by the light receiver, at which turbidity of the cell culture solution is measured.

Advantageous Effects of the Invention

In the present invention, a cell culture apparatus and a cell culture method can be provided each of which can continuously and accurately measure turbidity of a cell culture solution and culture a cell, without inserting a turbidity sensor from outside into a sterile bag.

EMBODIMENT FOR CARRYING OUT THE INVENTION

[Cell Culture Apparatus]

Next is described in detail an embodiment of the present invention with reference to accompanied drawings where appropriate.

Figure 1:
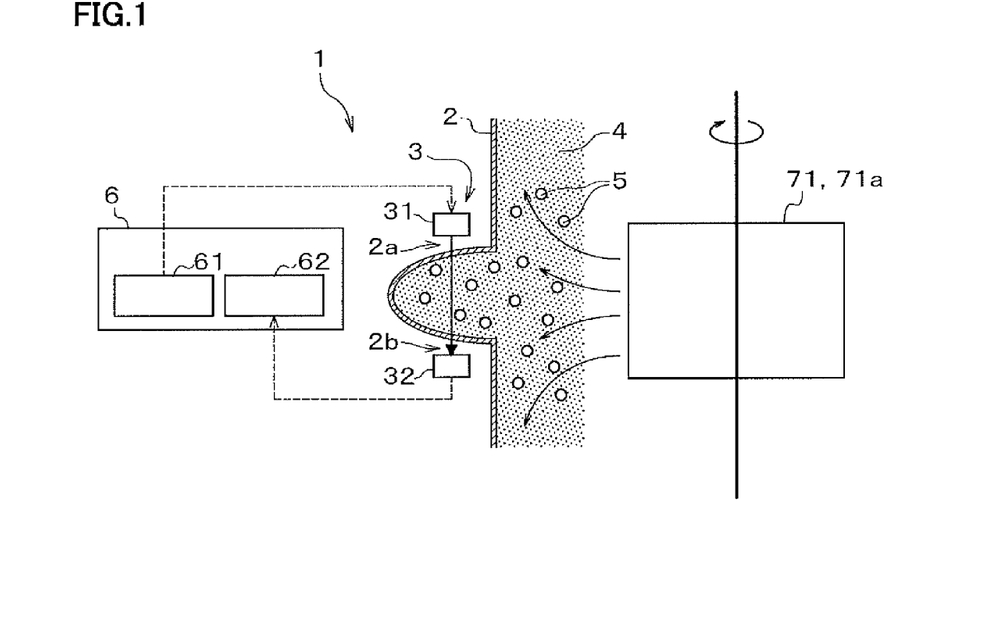
FIG. 1 is a schematic block diagram illustrating a basic concept of a cell culture apparatus according to an embodiment of the present invention.

FIG. 1 is a schematic block diagram illustrating a basic concept of a cell culture apparatus according to an embodiment of the present invention.

As illustrated in FIG. 1, a cell culture apparatus 1 includes a sterile bag 2 and a turbidity sensor 3. The cell culture apparatus 1 can be applied to culture microorganisms which produce substances as main materials of pharmaceutical products, health foods, and the like, or to culture animal or plant cells.

The sterile bag 2 is flexible and transparent and is installed at a prescribed position in the cell culture apparatus 1. A cell culture solution 4 is cultured in the sterile bag 2. The sterile bag 2 which can be used herein is, for example, a commercially-available single-use bag which is made of an ethylene vinyl acetate or ethyl vinyl alcohol multi-layer film for use in pharmaceutical products packaging. The sterile bag 2 is not, however, limited to the commercially-available one, and any bag which is made sterile by gamma rays or ethylene oxide gas can be suitably used.

The cell culture solution 4 used herein is a culture liquid in which a cell is being cultured or which is ready for culturing a cell after being subjected to a prescribed preliminary process. That is, the cell culture solution 4 is a culture solution containing a cell cultured or to be cultured. Note that a liquid medium used herein is a medium which is ready for culturing but to which a cell has not yet been added (or seeded or sown).

The cell 5 used herein for culturing includes, for example, an animal cell, a plant cell, a photosynthesis bacterium, a microalga, a cyanobacteria, an insect cell, a bacterium, a yeast, a fungus, and an alga. The animal cell which produces a protein such as an antibody and an enzyme is in particular suitable herein. Any liquid medium used for culturing a cell can be used as long as being suited for the cell to be cultured, and the liquid medium is not limited to of specific type.

A substance produced in this embodiment by culturing the cell 5 includes, for example, but is not limited to, a protein such as an antibody and an enzyme, a physiologically active substance such as a low-molecular compound and a high-molecular compound, a virus, a carotenoid such as beta-carotene and astaxanthin, a pigment such as chlorophyll and bacterio-chlorophyll, and a phycobilin protein such as phycocyanin used for coloring food, beverage, cosmetics, or the like, and a physiologically active substance such as a fatty acid.

The turbidity sensor 3 described above includes a light emitter 31 and a light receiver 32.

The light emitter 31 emits light to the cell culture solution 4 in the sterile bag 2 via a portion 2a of the sterile bag 2. The light emitter 31 is connected to a control unit 61. The control unit 61 controls an amount of light emitted from a light source of the light emitter 31.

The light receiver 32 receives the light transmitted through the cell culture solution 4 in the sterile bag 2 via another portion 2b of the sterile bag 2. The light receiver 32 is connected to a computation unit 62. Though described later with reference to FIG. 4 and FIG. 6, the computation unit 62 is connected to a stirring mechanism 71, a temperature regulation mechanism (not shown), a gas vent mechanism 72, and an automatic addition mechanism (not shown) of a medium component of a liquid medium, via a culture controller. The computation unit 62 is configured to calculate a concentration of the cells 5 in the cell culture solution 4, from a measurement value measured by the light receiver 32. Based on a result of the calculation, the culture controller 7 is configured to make the above-described mechanisms operate and control at least one of: a rotational speed of a stirring impeller 71a in the cell culture solution 4; a temperature of the cell culture solution 4; an amount of vented gas from a vent sparger 72a; and the medium component of the liquid medium. Note that the control unit 61 and the computation unit 62 are included in a turbidity detector 6.

In the cell culture apparatus 1 illustrated in FIG. 1, the light emitter 31 and the light receiver 32 are placed facing to each other; and the light emitter 31 emits light, which is made incident via the portion 2a of the sterile bag 2 into the cell culture solution 4 in the sterile bag 2. The light then transmits through the cell culture solution 4, proceeds straight through another portion 2b of the sterile bag 2 without changing a direction thereof, and is received by the light receiver 32. That is, the turbidity sensor 3 is configured to place the light emitter 31, the portion 2a of the sterile bag 2, another portion 2b of the sterile bag 2, and the light receiver 32, optically on a same straight line. Note that the terms "placed optically on a same straight line" used herein mean not only that the above-described constituents are arranged literally on the same straight line. Even when those constituents are not structurally placed on the same straight line, the terms also include that the constituents are placed such that the light emitted from the light emitter 31 is received by the light receiver 32 via the portion 2a and another portion 2b of the sterile bag 2, using a member for changing a direction of a path of the light, such as a mirror plane, a rectangular prism, and a pentagonal prism, which will be described hereinafter.

The structure as described above in which the sterile bag 2 is sandwiched between the light emitter 31 and the light receiver 32 facilitates measurement of turbidity of the cell culture solution 4 in the sterile bag 2. Thus, respective surfaces of the light emitter 31 and the light receiver 32 with each of which the sterile bag 2 comes into contact are, for example, made flat or equipped with transparent plates (not shown). A suitable range of a distance between the contact surfaces facing to each other, that is, a light path length of the light transmitting through the cell culture solution 4 is typically 1 to 100 mm and is preferably 5 to 50 mm, though varying depending on a wavelength of the light emitted from the light emitter 31, a concentration of the cultured cell 5, and a detection sensibility of the light receiver 32. The transparent plate used herein includes, for example, an acrylic plate, a glass plate, and a polycarbonate plane. Those plates suitably have high transparency and also high mechanical strength.

The light source (not shown) of the light emitter 31 used herein includes various industrial light sources, such as, for example, a light source having wavelengths of continuous spectrum including an incandescent lamp and a halogen lamp, and a light source containing a specific wavelength including a semiconductor laser and an LED. The control unit 61 connected to the light emitter 31 controls an amount of light emitted from the light source.

In selecting a wavelength of the light emitted from the light emitter 31, the shorter the better, because light scattering is typically greater in a shorter wavelength region, and detection sensitivity of turbidity becomes larger. In a case where a cell or a culture medium contains a pigment or the like having an absorption band in a specific wavelength region, however, the light emitter 31 preferably emits light of a wavelength different from that in the absorption band. Note that light in an ultraviolet region of a wavelength shorter than 400 nm is not preferable because protein, lipid, or the like contained in a cell is absorbed. On the other hand, in an infrared light region of a wavelength longer than 800 nm, turbidity caused by scattering is lowered, and such a wavelength is not preferable in terms of the detection sensitivity. It is thus preferable to select wavelength, for example, from 550 nm to 800 nm as the wavelength of the light emitted from the light emitter 31. If the cell culture solution 4 has a characteristic of a relatively flat absorption spectrum in the preferable wavelength region, a light source which emits light into a broad wavelength region is suitably used. On the other hand, if the cell culture solution 4 has a characteristic of a relatively non-flat absorption spectrum in the above-mentioned wavelength region, a light having a specific wavelength in a wavelength region in which no absorption peak and no absorption band is present is preferably selected. If, for example, a white light source is used as a light source of the light emitter 31, the light source can be configured to emit light having a specific wavelength, using an optical filter or the like.

As a light receiving element of the light receiver 32 which receives the light emitted from the light emitter 31, any light receiving element can be suitably used as long as the element is sensitive to light at a specific wavelength emitted from the light source, can convert a received light signal into an electrical signal, and can output an amount of the received light. A photodiode, a phototransistor, or the like can be typically used, but is not limited to, as the light receiving element.

With the light emitter 31 and the light receiver 32 as described above, light scattering which is caused by the cell 5 suspended in the cell culture solution 4 attenuates an amount of transmitting light. At this time, an amount of the attenuated light shows a certain correlation with a cell concentration. As described above, the light receiver 32 is connected to the computation unit 62. The light receiver 32: calculates a turbidity of the cell culture solution 4 from an amount of the light received; and transmits the calculated result to the computation unit 62. The computation unit 62 is configured to previously store therein a correlation coefficient between a cell concentration and a turbidity, thus allowing the computation unit 62 to calculate the cell concentration. The correlation coefficient described above varies depending on the cultured cell 5. It is preferable to set an appropriate correlation coefficient or the like based on a preliminary test or literature search.

When the cell 5 is multiplied after starting a culture, fragments of dead cells or cell contents such as protein and lipid may be accumulated in the cell culture solution 4, some of which adhere to an inner wall of the sterile bag 2. If those substances adhere to a light path between the light emitter 31 and the light receiver 32, an amount of transmitting light is attenuated, which increases an apparent turbidity. The cell concentration is therefore calculated to be larger than it actually is. In an area where the cell culture solution 4 flows little or is stagnant, the cell concentration in the area is calculated to be different from an average in the sterile bag 2. Thus, in order to reduce those influences, it is preferable to place each of a stirring mechanism 71 in the sterile bag 2 and the turbidity sensor 3 (the light emitter 31 and the light receiver 32) in a position where the cell culture solution 4 has a high fluidity by the stirring mechanism 71. Note that the stirring mechanism 71 illustrated in FIG. 1 is a stirring impeller 71a which includes a shaft member equipped with a plurality of blades, as an example. The stirring mechanism 71 used herein may be a magnetic stirrer or the like. If the magnetic stirrer is used which directly comes in contact with the sterile bag 2, it is preferable to reinforce a possible contact portion of the sterile bag 2 using a fluorine resin member or the like, so as not to damage the sterile bag 2.

As described above, the cell culture apparatus 1 may include the stirring impeller 71a or a shaking mechanism (not shown) so as to stir the cell culture solution 4. The cell culture apparatus 1 may not, however, include those mechanisms if it is not desirable to stir the cell 5. That is, the mechanisms are used optionally. When the stirring impeller 71a or the shaking mechanism is operated, it is preferable that the computation unit 62 is configured to: calculate a concentration of the cell 5 in the cell culture solution 4, from a measurement value measured by the light receiver 32; and control a stirring or shaking speed based on the calculated result, because the configuration makes it possible to continue the culture suitably.

It is more preferable that the computation unit 62 is configured to control, in addition to the stirring speed or the like, a temperature of the cell culture, an amount of vented gas, a medium component of a liquid medium, and the like, based on the above-described calculated result, because the configuration makes it possible to continue the culture more suitably.

The basic concept of the cell culture apparatus 1 according to this embodiment has been described above with reference to FIG. 1.

As described above, the cell culture apparatus 1 includes the turbidity sensor 3: that includes the light emitter 31 which emits light to the cell culture solution 4 in the sterile bag 2 via the portion 2a of the sterile bag 2, and the light receiver 32 which receives the light transmitted through the cell culture solution 4 in the sterile bag 2 via another portion 2b of the sterile bag 2; and that is configured to place the light emitter 31, the portion 2a of the sterile bag 2, another portion 2b of the sterile bag 2, and the light receiver 32, optically on the same straight line. The cell culture apparatus 1 measures turbidity of the cell culture solution 4 using the turbidity sensor 3 placed outside the sterile bag 2. In measuring the turbidity of the cell culture solution 4, this eliminates need for inserting the turbidity sensor 3 from outside to inside of the sterile bag 2 and also for sampling the cell culture solution 4. The cell culture apparatus 1 can thus eliminate a risk of causing contamination when the turbidity of the cell culture solution 4 is measured.

If the light emitter 31 and the light receiver 32 of the turbidity sensor 3 are placed in the position having high fluidity of the cell culture solution 4, little cell fragments or cell contents are accumulated. This can reduce an unfavorable apparent increase of the turbidity caused by attenuation of an amount of transmitting light. A stable turbidity measurement of cultured cells can be thus achieved even in a culture for a long period of time. In particular, turbidity of the cell culture solution 4 can be measured accurately in a single-use culture tank 21 of one-dimensional flat type or three-dimensional cylindrical type using the flexible and transparent sterile bag 2. Further, based on the measured turbidity of the cell culture solution 4, a cell concentration in the cell culture solution 4 can be measured without interruption. This allows an efficient control of the stirring speed and the temperature of the cell culture solution 4, supply of dissolved oxygen into the cell culture solution 4, and supply of a culture medium, depending on culture conditions of the cell 5. This results in a culture in good yield and allows an increase in the yield of a target culture product.

In the cell culture apparatus 1 according to this embodiment, as described above, optical turbidity in the flexible and transparent sterile bag 2 is measured in such a manner that the light emitter 31 and the light receiver 32 sandwich the sterile bag 2. This eliminates need for placing a reflecting mirror or the like and a member for installing the same, in the single-use sterile bag 2. That is, the cell culture apparatus 1 can be provided with a simple configuration at low cost.

<Specific Aspect of Turbidity Sensor>

Figure 2:
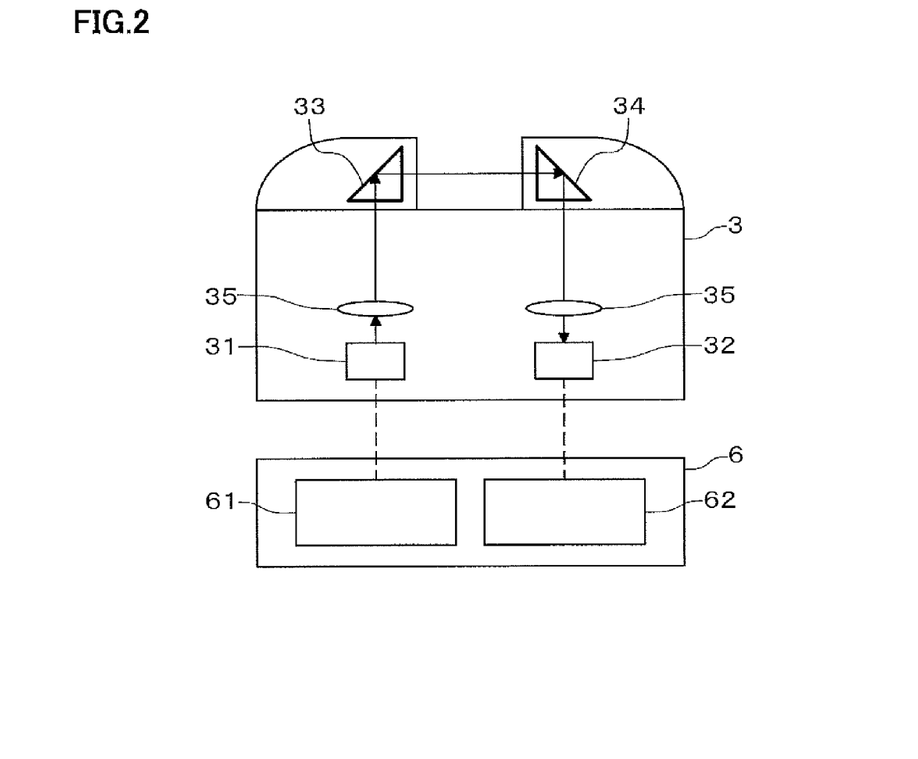
FIG. 2 is a schematic block diagram illustrating a specific aspect of a turbidity sensor for use in the cell culture apparatus according to the embodiment of the present invention.
Figure 3:
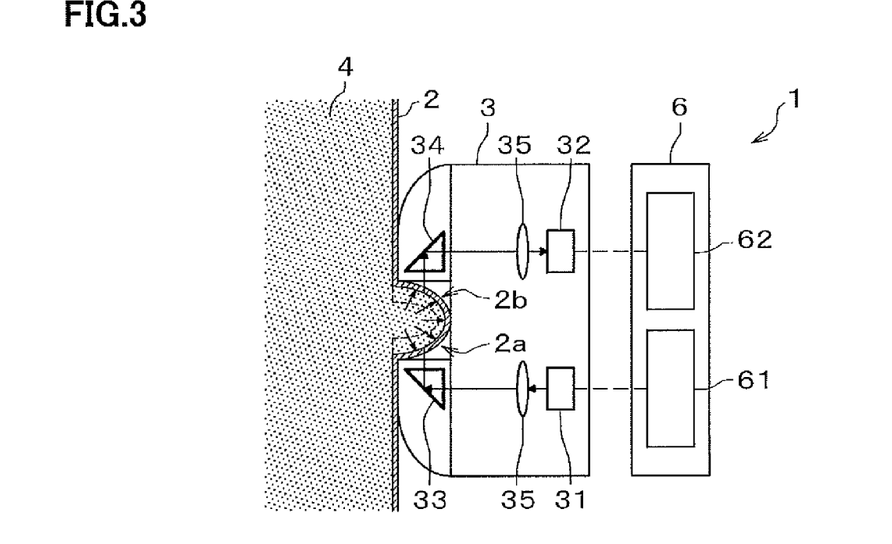
FIG. 3 is another schematic block diagram illustrating the specific aspect of the turbidity sensor for use in the cell culture apparatus according to the embodiment of the present invention.
Figure 4:
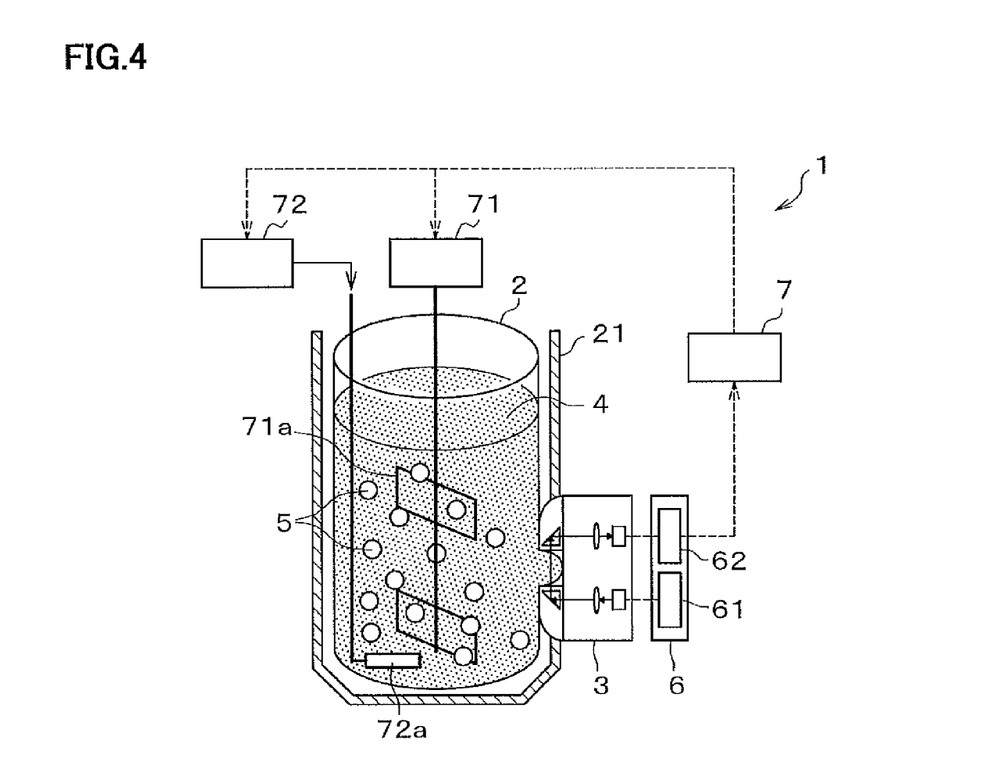
FIG. 4 is a still another schematic block diagram illustrating the specific aspect of the turbidity sensor for use in the cell culture apparatus according to the embodiment of the present invention.

Next is described a specific configuration of the cell culture apparatus 1 to which the above-described basic concept is applied, with reference to FIG. 2 to FIG. 4. In the description, same reference numerals are given to the above explained constituents, and description thereof is omitted herefrom.

FIG. 2 to FIG. 4 are each a schematic block diagram illustrating a specific aspect of the turbidity sensor 3 used for the cell culture apparatus 1 according to the embodiment of the present invention.

As illustrated in FIG. 2, the light emitter 31 of the turbidity sensor 3 is equipped with a first light path changer 33, and the light receiver 32 thereof includes a second light path changer 34.

The first light path changer 33 changes a direction of a path of light from a light source by 90 degrees, to thereby emit the light to the cell culture solution 4. The second light path changer 34 changes a direction of a path of the light which has been changed by the first light path changer 33 and has transmitted through the cell culture solution 4, by further 90 degrees, to thereby make the light receiver 32 receive the light with the path thereof having been changed twice. That is, the turbidity sensor 3 is configured to place the light emitter 31, the portion 2a of the sterile bag 2, another portion 2b of the sterile bag 2, and the light receiver 32, optically on the same straight line. Each of the first light path changer 33 and the second light path changer 34 suitably used herein includes, for example, a mirror plane, a rectangular prism, and a pentagonal prism.

As illustrated in FIG. 2, a recessed portion: has a pair of facing surfaces which face to each other; and is placed along the light path between the first light path changer 33 and the second light path changer 34. In this embodiment, the portions 2a, 2b of the sterile bag 2 in which the cell culture solution 4 is cultured is made to be put (or sandwiched) in the recessed portion as they are. That is, as illustrated in FIG. 3, the portions 2a, 2b of the sterile bag 2 are first set up such that the portion 2a is brought close to the first light path changer 33 and another portion 2b is brought close to the second light path changer 34. Then, at a start of culturing, the sterile bag is filled with the cell culture solution 4 to which prescribed amounts of a liquid medium and the cell 5 are added. This allows a close contact of the portion 2a and another portion 2b of the sterile bag 2, with corresponding inner surfaces of the recessed portion placed between the first light path changer 33 and the second light path changer 34. In the above-described configuration, as explained in the basic concept, the light emitter 31 can emit light to the cell culture solution 4 in the sterile bag 2 via the portion 2a of the sterile bag 2, and the light receiver 32 can receive the light transmitting through the cell culture solution 4 in the sterile bag 2 via another portion 2b of the sterile bag 2. Thus, the cell 5 can be cultured while turbidity of the cell culture solution 4 is measured continuously and accurately, without need for inserting a turbidity sensor from outside into the sterile bag 2. Further, the turbidity of the cell culture solution 4 in the sterile bag 2 can be measured without need for taking (sampling) the cell culture solution 4 out of the sterile bag 2. This can eliminate a risk of causing contamination or the like.

Description of the specific aspect of the cell culture apparatus 1 is continued next. As illustrated in FIG. 2, in the cell culture apparatus 1, the light emitter 31 whose amount of light emitted from a light source thereof is controlled by the control unit 61 emits light on an upper side in the figure. The emitted light enters the first light path changer 33 via an optical lens 35. Note that the optical lens 35 can converge or diffuse light in accordance with intended usage. The optical lens 35 is provided optionally and may not be provided if not necessary. Though not shown in FIG. 2, in order to achieve a suitable path of light, for example, a portion which serves as the light path in the turbidity sensor 3 can be designed to be hollow, or an optical fiber or an optical waveguide can be used for forming the light path.

The first light path changer 33 totally reflects the light having been made incident into the first light path changer 33, to thereby change a direction of a light path of the reflected light by 90 degrees. In FIG. 2, the first light path changer 33 changes the light path in a right direction. If a right-angle prism or a pentaprism is used as the first light path changer 33, it is preferable to arrange a hollow space on at least a back side of the total reflection surface and adjust a difference between refractive indexes of the hollow space and a member constituting the prism, to thereby increase efficiency of the total reflection. The prism may be coated with aluminum or metal film, so as to increase reflectivity. The light whose light path has been changed by the first light path changer 33 exits from one of the facing surfaces of the recessed portion nearer to the first light path changer 33, and enters the other facing surface. The second light path changer 34 totally reflects the light having been entered the other facing surface, whose light path is changed by 90 degrees. In FIG. 2, the light path is changed on a lower side in the figure by the second light path changer 34. In this case, it is preferable that the second light path changer 34 is also configured similarly to the first light path changer 33. The light whose light path has been changed by the second light path changer 34 is received by the light receiver 32 via the optical lens 35. The light receiver 32 having received the light converts the received light signal into an electrical signal, and quantitatively outputs an amount of the received light to the computation unit 62 of the turbidity detector 6.

Each of the first light path changer 33 and the second light path changer 34 changes the direction of the light path as described above. It is thus required that respective optical axes thereof are accurately aligned. Though the first light path changer 33 and the second light path changer 34 are illustrated as separate constituents in FIG. 2, it is preferable that the two changers 33, 34 are integrally formed as one unit, using, for example, transparent resin, so as to ensure accurate alignment of the optical axes.

When the turbidity sensor 3 illustrated in FIG. 2 is used, the sterile bag 2 is placed in a prescribed position in the cell culture apparatus 1; the turbidity sensor 3 is also placed in a prescribed position in the apparatus 1; and, after that, a liquid medium and the cell 5 are put in the sterile bag 2, as illustrated in FIG. 4. Note that the turbidity sensor 3 is preferably placed in a position where the cell culture solution 4 has a high fluidity. In the case illustrated in FIG. 4, the turbidity sensor 3 is preferably placed on extension lines of a rotation radius of the stirring impeller 71a. Further, if a volume of the sterile bag 2 is made slightly larger than that of the culture tank 21, the sterile bag 2 is closely brought in contact with the recessed portion of the turbidity sensor 3 when the liquid medium is put therein. This advantageously prevents gas phase from being contained along the light path when the turbidity of the cell culture solution 4 is measured, thus allowing a more accurate measurement of the turbidity.

As illustrated in FIG. 4, in the cell culture apparatus 1 using the turbidity sensor 3 described above, the computation unit 62 is configured to calculate a concentration of the cell 5 in the cell culture solution 4, from a measurement value measured by the light receiver 32 of the turbidity sensor 3. The cell culture apparatus 1 controls at least one of the stirring mechanism 71, the temperature regulation mechanism (not shown), the gas vent mechanism 72, and the automatic addition mechanism (not shown) of the medium component of the liquid medium, based on the calculated result. Control of those mechanisms is preferably provided by, for example, the culture controller 7. As illustrated in FIG. 4, the culture controller 7: transmits an appropriate control signal to the stirring mechanism 71 and the gas vent mechanism 72; and thereby controls the number of stirring rotations of the stirring impeller 71a and a quantity of vented gas from the vent sparger 72a, based on a result of the calculation using a program previously incorporated therein. This makes it possible to, in response to proliferation of the cell 5 by culturing, maintain appropriate flow stirring and concentrations of dissolved oxygen and dissolved carbon dioxide, thus allowing efficient culturing. Though not illustrated in the figure, the culture tank 21 includes a temperature regulation mechanism equipped with a jacket or a pettier device for making constant-temperature water circulate therein. The culture controller 7 controls the temperature regulation mechanism (not shown) and thereby regulates a culture temperature. The culture controller 7 can be realized by a commercially available PC (personal computer) with a program for controlling a culture incorporated therein.

<Another Specific Aspects of Turbidity Sensor>

Figure 5:
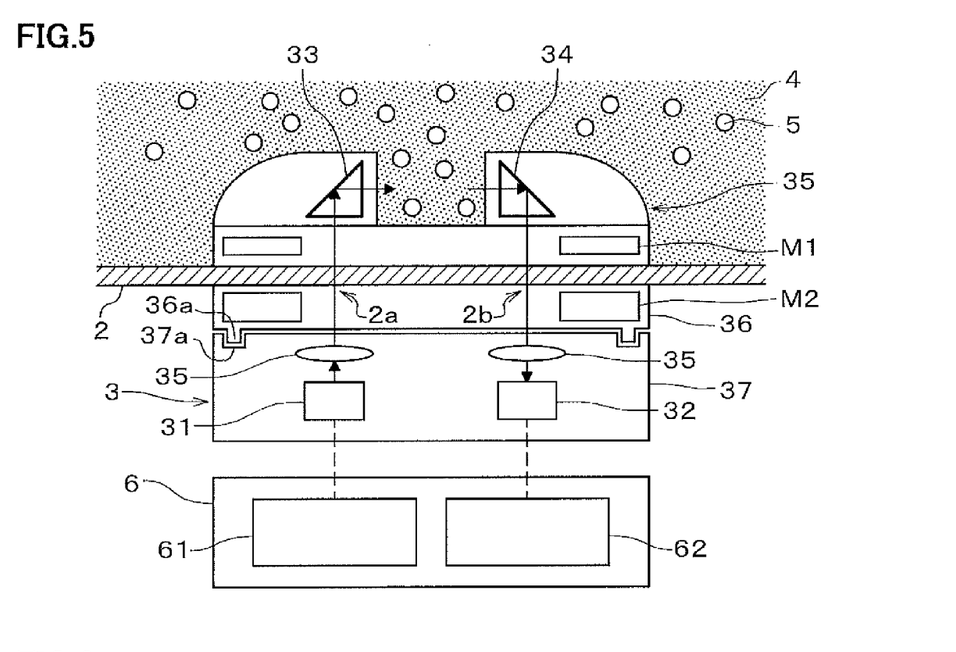
FIG. 5 is a schematic block diagram illustrating another specific aspect of the turbidity sensor for use in the cell culture apparatus according to the embodiment of the present invention.
Figure 6:
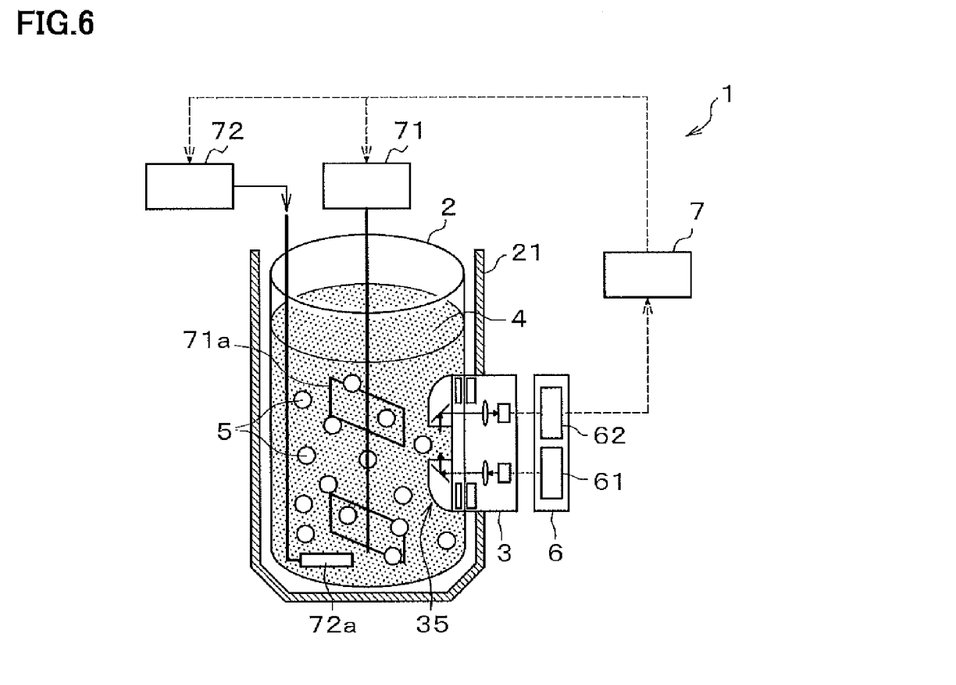
FIG. 6 is another schematic block diagram illustrating another specific aspect of the turbidity sensor for use in the cell culture apparatus according to the embodiment of the present invention.

Next is described another specific aspect of the turbidity sensor 3 used in the cell culture apparatus 1 according to the embodiment of the present invention, with reference to FIG. 5 and FIG. 6. In the description, same reference numerals are given to the constituents explained above, and description thereof is omitted herefrom.

FIG. 5 and FIG. 6 are each a schematic block diagram illustrating another specific aspect of the turbidity sensor 3 used for the cell culture apparatus 1 according to the embodiment of the present invention.

The turbidity sensor 3 illustrated in FIG. 5 includes the first light path changer 33 and the second light path changer 34 which are same as those of the turbidity sensor 3 explained above with reference to FIG. 2 to FIG. 4. The turbidity sensor 3 illustrated in FIG. 5 is, however, different from that described above in a configuration of measuring turbidity via the sterile bag 2 and an order in which the light path is directed. Note that, the turbidity sensor 3 illustrated in FIG. 5 is also configured to place the light emitter 31, the portion 2a of the sterile bag 2, another portion 2b of the sterile bag 2, and the light receiver 32 optically on the same straight line.

As illustrated in FIG. 5, the turbidity sensor 3 according to this embodiment includes, inside the sterile bag 2, a light path change unit 39 which includes the first light path changer 33 and the second light path changer 34. The turbidity sensor 3 also includes, outside the sterile bag 2, the light emitter 31 and the light receiver 32. The turbidity detector 6 which is also placed outside the sterile bag 2 includes the control unit 61 and the computation unit 62. The configuration makes it possible to, in installing the light path change unit 39 inside the sterile bag 2, minimize the number of members constituting the light path change unit 39 which are to be disposed of after culturing. In addition, if the light path change unit 39 is manufactured of low cost material such as plastic, further cost reduction can be realized.

With the configuration described above, as illustrated in FIG. 5, the first light path changer 33 can: receive light from the light source of the light emitter 31 thereinto via the portion 2a of the sterile bag 2; change a direction of a path of the received light, and emit the light to the cell culture solution 4.

Further, the second light path changer 34 can: receive the light whose light path has been changed by the first light path changer 33 and has been emitted through the cell culture solution 4; change a direction of the path of the received light; and emit the light to the light receiver 32 via another portion 2b of the sterile bag 2.

As explained above in the basic concept, the light emitter 31 can emit light to the cell culture solution 4 in the sterile bag 2 via the portion 2a of the sterile bag 2, and the light receiver 32 can receive the light transmitting through the cell culture solution 4 in the sterile bag 2 via another portion 2b of the sterile bag 2. Thus, the cell 5 can be cultured while turbidity of the cell culture solution 4 is measured continuously and accurately, without need for inserting a turbidity sensor from outside to inside of the sterile bag 2. Further, the turbidity of the cell culture solution 4 in the sterile bag 2 can be measured without need for taking (sampling) the cell culture solution 4 out of the sterile bag 2. This can eliminate a risk of causing contamination or the like when the turbidity is measured, because the light path change unit 39 placed inside the sterile bag 2 is subjected to, as a matter of course, sterilization treatment similar to that for the sterile bag 2.

In this case, it is preferable that an alignment of an axis of the light which is made to enter the first light path changer 33 from the light emitter 31 via the portion 2a of the sterile bag 2, and an alignment of an axis of the light which is made to enter the light receiver 32 from the second light path changer 34 via another portion 2b of the sterile bag 2, are performed as explained below. For example, the alignments are achieved by attraction-fixing a first magnetic member M1 placed in the light path change unit 39 and a second magnetic member M2 placed in the turbidity sensor 3. The magnetic member used herein includes, for example, a commonly-used magnetic member made of iron, cobalt, nickel, or an alloy thereof as well as a plastic magnetic material member manufactured by molding and solidifying metal magnetic powder using rubber or plastic. This makes it possible to, even when the cell culture solution 4 is stirred, the culture can be suitably continued without the light path change unit 39 being inconveniently separated from the other part of the turbidity sensor 3.

When the turbidity sensor 3 illustrated in FIG. 5 equipped with the second magnetic member M2, it is preferable that the turbidity sensor 3 is configured to be separable into a base 36 including the second magnetic member M2 and a main unit 37 including the light emitter 31 and the light receiver 32. This can reduce cost, because, even when magnetic force of the second magnetic member M2 becomes weak, it is just required to exchange only the low-priced base 36 for a new one, while the relatively high-priced main unit 37 which includes the light emitter 31 and the light receiver 32 can still be used. The base 36 and the main unit 37 preferably have respective engagement mechanisms for alignment with each other. The engagement mechanism for alignment is realized by, for example, a concave portion 37a and a convex portion 36b which have shapes corresponding to each other at prescribed positions in the respective members. This makes it possible to accurately perform the alignment of the axis of the light which is made to enter the first light path changer 33 from the light emitter 31 via the portion 2a of the sterile bag 2, and the alignment of the axis of the light which is made to enter the light receiver 32 from the second light path changer 34 via another portion 2b of the sterile bag 2. Note that a width of light suitably used in the present invention is 2 to 4 mm, because the present invention is made with an intention of measuring turbidity of the cell culture solution 4. Thus, a slight deviation of the light axis will not negatively affect the measurement.

As illustrated in FIG. 6, the computation unit 62 of the cell culture apparatus 1 using the turbidity sensor 3 described above is connected to the culture controller 7. Similarly to the cell culture apparatus 1 illustrated in FIG. 4, the culture controller 7 can culture the cell 5 while controlling at least one of the stirring mechanism 71, the temperature regulation mechanism (not shown), the gas vent mechanism 72, and the automatic addition mechanism (not shown) of a medium component of a liquid medium.

<Variations of Light Path>

Next are described variations of the light path described above, with reference to FIG. 7 and FIG. 8. In the description, same reference numerals are given to the constituents already explained above, and description thereof is omitted herefrom.

Figure 7:
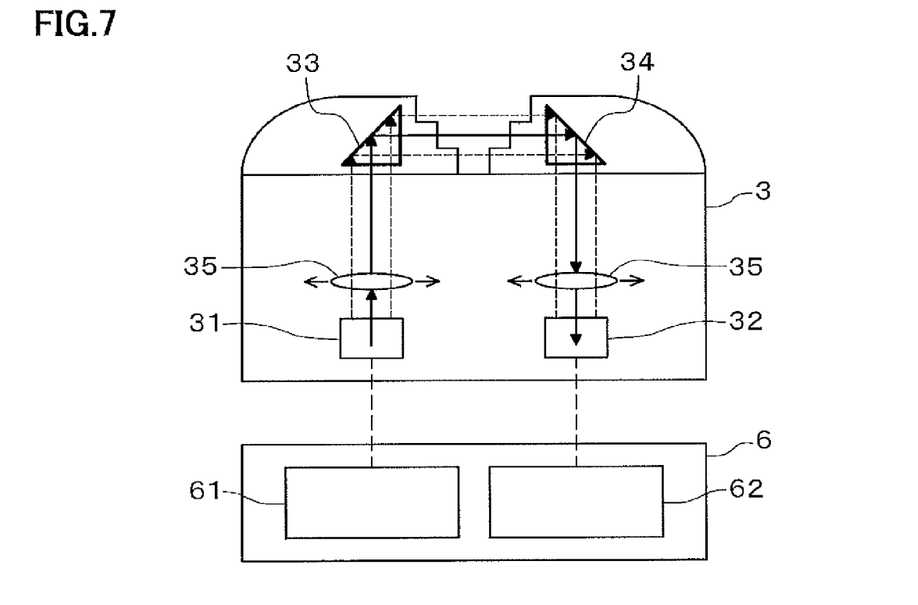
FIG. 7 is a schematic block diagram illustrating a light path according to a variation of the present invention.
Figure 8:
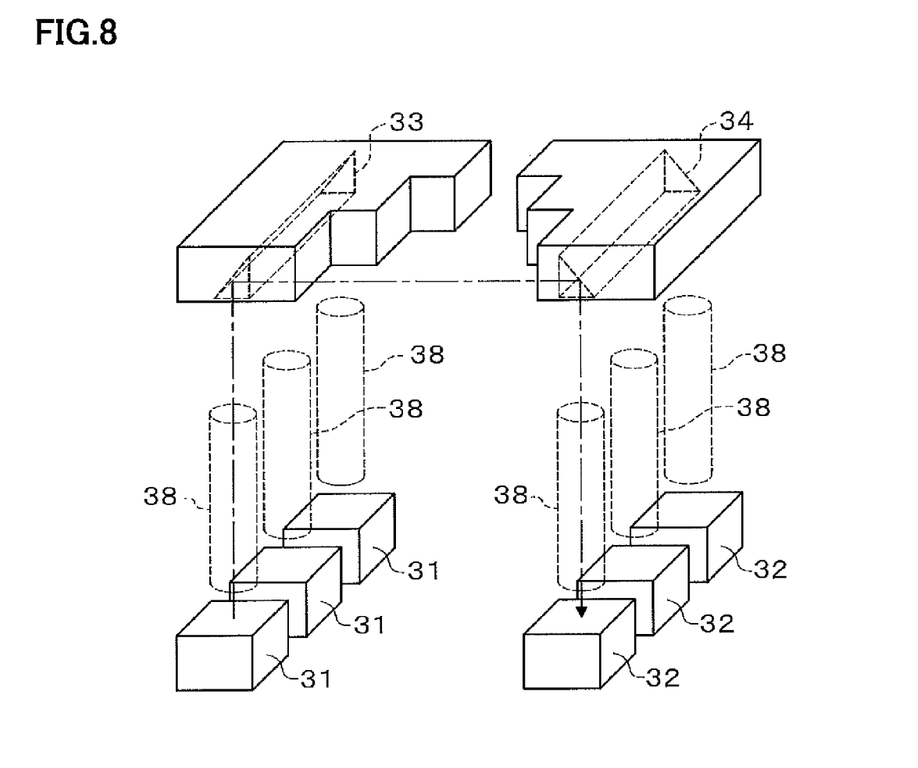
FIG. 8 is a schematic block diagram illustrating a light path according to another variation of the present invention.

FIG. 7 is a schematic block diagram illustrating a light path according to a variation. FIG. 8 is a perspective diagram illustrating a light path according to another variation.

A cell concentration is typically increased along with culturing, and turbidity of the cell culture solution 4 is largely changed. Detection accuracy of the turbidity depends on emission intensity of the light emitter 31 and reception sensitivity of the light receiver 32, as well as a length of a path of light which transmits through the cell culture solution 4 and is used for measuring the turbidity (a light path length). Even with a constant cell concentration, if the light path length is made larger, intensity of the light transmitted and reaching the light receiver 32 becomes smaller. Hence, accuracy in calculating the turbidity and the cell concentration can be improved in such a manner that, when the cell concentration is low at an early stage of a culture, the light path length is made large, and, when the cell concentration becomes high at a later stage thereof, the light path length is made small.

In the example illustrated in FIG. 7, in order to improve accuracy in calculating the turbidity and the cell concentration, at least one of a pair of opposing surfaces between the first light path changer 33 and the second light path changer 34 is made to be a stepped surface. With this configuration, a plurality of light path lengths of the light transmitting through the cell culture solution 4 can be provided. Note that, in the variation illustrated in FIG. 7, both of the opposing surfaces are made to be stepped. A position in which the light emitted from the light emitter 31 is reflected by the first light path changer 33 can be changed by shifting the optical lens 35 in a direction perpendicular to the light. Also, the light receiver 32 can appropriately receive the light reflected by the second light path changer 34, by shifting the optical lens 35 in a direction perpendicular to the light. With the configuration of the light path, as described above, when a cell concentration is low at an early stage of a culture, the light path length can be made large, and, when the cell concentration is high at a later stage thereof, the light path length can be made small. This can improve accuracy in calculating the turbidity and the cell concentration. Note that the optical lens 35 can be shifted using an electric motor or an actuator such as a piezoelectric device.

Another variation illustrated in FIG. 8 is same as the variation illustrated in FIG. 7 in that at least one of a pair of the opposing surfaces between the first light path changer 33 and the second light path changer 34 is made to be a stepped surface. Another variation illustrated in FIG. 8 is, however, different from the variation illustrated in FIG. 7 in that: respective length dimensions of the first light path changer 33 and the second light path changer 43 are made larger; and a plurality of the light emitters 31 and a plurality of the light receivers 32 are provided (in FIG. 8, three units of each of the constituents 31, 32). Another variation illustrated in FIG. 8 is also different from the variation illustrated in FIG. 7 in that a plurality of the light paths having different lengths are arranged in a longitudinal direction in the figure. Even with this configuration of the light paths, as described above, when a cell concentration is low at an early stage of a culture, the light path length can be made large, and, when the cell concentration is high at a later stage thereof, the light path length can be made small. This can improve accuracy in calculating the turbidity and the cell concentration.

In both the variation illustrated in FIG. 7 and another variation illustrated in FIG. 8, an appropriate light path length and the light emitter 31 and the light receiver 32 corresponding thereto can be selected for measurement of turbidity, depending on a range in which a cell concentration varies in a course of culturing. In addition, when all of the light emitters 31 and the light receivers 32 are operated simultaneously, respective plural values of the turbidity measured based on different light path lengths and the calculated cell concentration can be obtained. By calculating an average value of the obtained cell concentrations, accuracy of control can be improved.

In another variation illustrated in FIG. 8, it is preferable to divide light into a plurality of light beams in respective light paths using optical waveguides 38 illustrated in FIG. 8, so as to prevent the lights in the respective light paths from acting on one another and from reducing measurement accuracy. The optical waveguide 38 used herein preferably incorporates a structure capable of transmitting light without loss by making use of optical fiber or total reflection at an interface between a core and a clad having different refractive indexes from each other. In this case, the structure may be made of, for example, an inorganic material such as quartz glass and silicon, and an organic material such as high-purity polyimide resin, polyamide resin, and polyether resin. If the optical lens 35 is appropriately selected and can successfully obtain parallel beams of light, the optical waveguide 38 used herein may be the optical waveguide 38 having a tunnel-shaped hollow therein.

[Cell Culture Method]

Next is described a cell culture method according to the embodiment of the present invention.

The cell culture method according to the embodiment includes a setting step and a culture step.

<Setting Step>

The setting step is a step of setting, in respective prescribed positions in the cell culture apparatus 1: the sterile bag 2 that is flexible and transparent; and the turbidity sensor 3 that includes the light emitter 31 which emits light into the cell culture solution 4 in the sterile bag 2 via the portion 2a of the sterile bag 2, and the light receiver 32 which receives the light having passed through the cell culture solution 4 in the sterile bag 2 via another portion 2b of the sterile bag 2, and that is configured to place the light emitter 31, the portion 2a of the sterile bag 2, another portion 2b of the sterile bag 2, and the light receiver 32 optically on the same straight line. Description of the sterile bag 2 and the turbidity sensor 3 has already been made above and is thus omitted herefrom.

The sterile bag 2 is preferably set in the culture tank 21 as illustrated in FIG. 4 or FIG. 6. This is because the sterile bag 2 is like a flexible plastic bag and is not high in shape-retaining property or strength when a liquid medium is put thereinto. The culture tank 21 used herein is suitably made of metal such as stainless steel and aluminum.

<Culture Step>

The culture step is a step of putting and culturing the cell culture solution 4 and the cell 5 inside the sterile bag 2 having been set in the setting step.

As described above, the cell 5 can be cultured under a condition suited for the cell 5.

In the culture step of the cell culture method according to this embodiment, the light emitter 31 of the turbidity sensor 3 emits light to the cell culture solution 4; the light receiver 32 receives the light passing through the cell culture solution 4 and measures turbidity of the cell culture solution 4; the computation unit 62 connected to the light receiver 32 calculates a concentration of the cell 5 in the cell culture solution 4, from a measurement value measured by the light receiver 32; and the culture controller 7 controls at least one of the stirring mechanism 71, the temperature regulation mechanism (not shown), the gas vent mechanism 72, and the automatic addition mechanism (not shown) of a medium component of a liquid medium, based on the calculated result. This makes it possible to, in response to proliferation of the cell 5 by culturing, maintain appropriate flow stirring and concentrations of dissolved oxygen and dissolved carbon dioxide, which allows efficient culturing.

Also in the cell culture method according to this embodiment, each of the light emitter 31 and the light receiver 32 is placed in a position where the cell culture solution 4 has high fluidity, similarly to the cell culture apparatus 1 described above.

Preferably, the light emitter 31 and the light receiver 32 used herein include the first light path changer 33 and the second light path changer 34, respectively. In this case, turbidity of the cell culture solution 4 is preferably measured in such a manner that the first light path changer 33 is closely brought in contact with the portion 2a of the sterile bag 2, and the second light path changer 34 is closely brought in contact with another portion 2b of the sterile bag 2 (see FIG. 2 to FIG. 4).

The first light path changer 33 is configured to: receive light emitted from a light source of the light emitter 31 via the portion 2a of the sterile bag 2; appropriately change a path of the light; and emit the light to the cell culture solution 4. The second light path changer 34 is configured to: receive the light whose path has been changed by the first light path changer 33 and which has then passed through the cell culture solution 4; appropriately change a path of the light; and make the light receiver 32 receive the light via another portion 2b of the sterile bag 2, to thereby measure the turbidity of the cell culture solution 4 (see FIG. 5 and FIG. 6).

The preferred aspects described above have already been explained in detail in the description of the cell culture apparatus 1, and duplicate description is omitted herefrom.

The cell culture apparatus and the cell culture method according to the embodiment of the present invention have been described above in detail. The present invention is, however, carried out not only by the above-described embodiment but also by various variations. For example, the above-described embodiment is intended to be illustrative of the present invention in an easily understandable manner and the present invention is not limited to that includes all of the constituents explained in the embodiment. Part of a configuration of the embodiment can be substituted by or added to that of another embodiment. Part of a configuration of the embodiment can be added with or substituted with a configuration of another embodiment.

The invention claimed is:

1. A cell culture apparatus comprising:
   a recessed portion having a pair of facing surfaces that face each other, the recessed portion being configured to receive between the pair of facing surfaces a portion of a cell culture solution in which cells are cultured, the cell culture solution being contained in a flexible and transparent sterile bag; and
   a turbidity sensor that includes:
      a light emitter which emits light to the cell culture solution in the sterile bag via a first portion of the sterile bag, and
      a light receiver which receives the light that has been transmitted through the cell culture solution in the sterile bag via a second portion of the sterile bag,
   wherein:
   the light is transmitted along a light path comprising the light emitter, the first portion of the sterile bag, the second portion of the sterile bag, and the light receiver in this order;
   a space between the pair of facing surfaces constitutes a part of the light path; and
   at least one of the pair of facing surfaces is a stepped surface.

2. The cell culture apparatus according to claim 1, further comprising a computation unit that is connected to the light receiver and that is configured to calculate a concentration of the cultured cells contained in the cell culture solution, from a measurement value measured by the light receiver, and, based on a result of the calculation, control at least one of a speed of stirring the cell culture solution, a temperature of the cell culture solution, an amount of vented gas, and a medium component of a liquid medium of the cell culture solution.

3. The cell culture apparatus according to claim 1, further comprising:
   a first light path changer, which is configured to change a direction of a path of the light that is emitted from a light source to transmit the light to the cell culture solution via the first portion of the sterile bag, and a second light path changer, which is configured to change a direction of a path of the light that has been transmitted through the cell culture solution and the second portion of the sterile bag to transmit the light to the light receiver, wherein the first portion and the second portion of the sterile bag are positioned in between the first light path changer and the second light path changer.

4. The cell culture apparatus according to claim 1, further comprising a light path change unit comprising a first light path changer and a second light path changer
wherein:
the first light path changer is configured to:
receive light from a light source of the light emitter via the first portion of the sterile bag,
change a direction of a path of the received light to transmit the light to the cell culture solution; and
the second light path changer is configured to:
receive the light whose light path direction has been changed by the first light path changer and has been transmitted through the cell culture solution, and
change a direction of the path of the received light to transmit the light to the light receiver via the second portion of the sterile bag.

5. The cell culture apparatus according to claim 4, further comprising:
a first magnetic member arranged in the light path change unit, and
a second magnetic member arranged in the turbidity sensor
wherein the first magnetic member and the second magnetic member are configured to perform an alignment of an axis of the light that enters the first light path changer from the light emitter via the first portion of the sterile bag, and an alignment of an axis of the light which enters the light receiver from the second light path changer via the second portion of the sterile bag.

6. The cell culture apparatus according to claim 5, wherein
the turbidity sensor is separable into a base including the second magnetic member and a main unit including the light emitter and the light receiver, and
the base and the main unit have respective engagement structures for alignment with each other.

7. The cell culture apparatus according to claim 1, wherein each of the light emitter and the light receiver is arranged in a position where the cell culture solution has a high fluidity.

8. The cell culture apparatus according to claim 1, wherein the recessed portion is arranged outside of the sterile bag and is configured to receive between the pair of facing surfaces a portion of the sterile bag containing the portion of the cell culture solution.

9. The cell culture apparatus according to claim 4, wherein
the recessed portion is arranged inside the sterile bag and comprises the light path change unit, and
the turbidity sensor is arranged outside the sterile bag.

10. A cell culture method comprising:
arranging a flexible and transparent sterile bag containing a cell culture solution in a prescribed position in a cell culture apparatus, a portion of the cell culture solution being positioned between a pair of facing surfaces of a recessed portion of the cell culture apparatus, the cell culture solution containing cells to be cultured; and
then culturing the cell culture solution inside the sterile bag; and
measuring turbidity of the cell culture solution by transmitting light from a light emitter of the cell culture apparatus through the portion of the cell culture solution positioned between the pair of facing surfaces of the recessed portion to a light receiver of the cell culture apparatus;
wherein
the light is transmitted along a light path comprising the light emitter, a first portion of the sterile bag, a second portion of the sterile bag, and the light receiver;
a space between the pair of facing surfaces constitutes a part of the light path; and
at least one of the pair of facing surfaces is a stepped surface.

11. The cell culture method according to claim 10, further comprising:
calculating via a computation unit connected to the light receiver a concentration of the cultured cells contained in the cell culture solution from a measurement value measured by the light receiver, and
controlling at least one of a speed of stirring the cell culture solution, a temperature of the cell culture solution, an amount of vented gas, and a medium component of a liquid medium of the cell culture solution based on the result of the calculation.

12. The cell culture method according to claim 10, wherein each of the light emitter and the light receiver is arranged in a position where the cell culture solution has a high fluidity.

13. The cell culture method according to claim 10, further comprising:
a first light path changer, which is configured to change a direction of a path of the light emitted from a light source to transmit the light to the cell culture solution via the first portion of the sterile bag, and
a second light path changer, which is configured to change the direction of a path of the light which has been transmitted through the cell culture solution and the second portion of the sterile bag to transmit the light to the light receiver,
wherein the first portion and the second portion of the sterile bag are in positioned between the first light path changer and the second light path changer.

14. The cell culture method according to claim 10, further comprising a light path change unit comprising a first light path changer and a second light path,
wherein
the first light path changer is configured to:
receive light from a light source of the light emitter via the first portion of the sterile bag, and
change a direction of a path of the received light to transmit the light to the cell culture solution, and
the second light path changer is configured to:
receive the light whose light path direction has been changed by the first light path changer and has been transmitted through the cell culture solution, and
change a direction of the path of the received light to transmit the light to the light receiver via the second portion of the sterile bag.

* * * * *